United States Patent
Sone

(10) Patent No.: US 9,749,564 B2
(45) Date of Patent: Aug. 29, 2017

(54) ENDOSCOPE SYSTEM

(71) Applicant: OLYMPUS CORPORATION, Tokyo (JP)

(72) Inventor: Shingo Sone, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/182,833

(22) Filed: Jun. 15, 2016

(65) Prior Publication Data

US 2016/0295141 A1 Oct. 6, 2016

Related U.S. Application Data

(63) Continuation of application No. PCT/JP2015/066323, filed on Jun. 5, 2015.

(30) Foreign Application Priority Data

Jun. 10, 2014 (JP) .................................. 2014-119753

(51) Int. Cl.
*A61B 1/04* (2006.01)
*H04N 5/369* (2011.01)
(Continued)

(52) U.S. Cl.
CPC ....... *H04N 5/3698* (2013.01); *A61B 1/00009* (2013.01); *A61B 1/00045* (2013.01);
(Continued)

(58) Field of Classification Search
CPC .... H04N 19/14; H04N 5/3765; H04N 5/3698; A61B 1/04; A61B 1/00114; A61B 1/00009; A61B 1/00045; G02B 23/26
See application file for complete search history.

(56) References Cited

U.S. PATENT DOCUMENTS

| | | | |
|---|---|---|---|
| 4,697,208 A | 9/1987 | Eino | |
| 2011/0025907 A1* | 2/2011 | Tsuda | H04N 5/23203 348/372 |
| 2013/0041220 A1* | 2/2013 | Kutsuma | A61B 1/00009 600/109 |

FOREIGN PATENT DOCUMENTS

| | | |
|---|---|---|
| JP | H04-6306 B2 | 2/1992 |
| JP | H06-311440 A | 11/1994 |

(Continued)

OTHER PUBLICATIONS

International Search Report dated Sep. 8, 2015 issued in PCT/JP2015/066323.

*Primary Examiner* — Behrooz Senfi
(74) *Attorney, Agent, or Firm* — Scully, Scott, Murphy & Presser, P.C.

(57) ABSTRACT

An endoscope system includes an image pickup section provided with an image sensor and configured to obtain an examination image; a cable that transmits the examination image; and a processor that receives the examination image, performs image processing, and displays the processed image. The processor includes: a cable driver that applies a voltage higher than an input voltage standard of the image pickup section so as to compensate for attenuation of a high-frequency signal caused by the cable and outputs a clock signal for driving the image pickup section; a peaking circuit that performs waveform correction of the clock signal; and a DC level limiting circuit configured to limit, when a clock signal inputted from the first peaking circuit is switched to a DC voltage, an amplitude level of the DC voltage so as not to exceed a level of the input voltage standard of the image pickup section.

6 Claims, 11 Drawing Sheets

(51) Int. Cl.
*G02B 23/26* (2006.01)
*H04N 7/18* (2006.01)
*A61B 1/00* (2006.01)
*H04N 5/372* (2011.01)
*H04N 5/376* (2011.01)
*H04N 5/225* (2006.01)

(52) U.S. Cl.
CPC ............ *A61B 1/00114* (2013.01); *A61B 1/04* (2013.01); *G02B 23/26* (2013.01); *H04N 5/372* (2013.01); *H04N 5/3765* (2013.01); *H04N 7/18* (2013.01); *H04N 2005/2255* (2013.01)

(56) References Cited

FOREIGN PATENT DOCUMENTS

| | | |
|---|---|---|
| JP | 2008-161427 A | 7/2008 |
| JP | 2013-165772 A | 8/2013 |

* cited by examiner

US 9,749,564 B2

ENDOSCOPE SYSTEM

CROSS REFERENCE TO RELATED APPLICATION

This application is a continuation application of PCT/JP2015/066323 filed on Jun. 5, 2015 and claims benefit of Japanese Application No. 2014-119753 filed in Japan on Jun. 10, 2014, the entire contents of which are incorporated herein by this reference.

BACKGROUND OF THE INVENTION

1. Field of the Invention

The present invention relates to an endoscope system, and more particularly to an endoscope system capable of supplying a driving signal of an appropriate voltage level to an image pickup section.

2. Description of the Related Art

An endoscope system which is provided with an endoscope that picks up an image of an object inside a subject to be examined, a processor that generates an observation image of the object whose image has been picked up with the endoscope, and the like has been widely used in medical fields and industrial fields.

A processor generates a driving signal for driving an image sensor provided in an image pickup section of an endoscope, and supplies the generated driving signal to the image sensor. For example, Japanese Patent Application Laid-Open Publication No. 2013-165772 discloses an endoscope apparatus that is capable of supplying a driving signal having an appropriate voltage level from an image pickup control section to an image pickup section.

In recent years, a driving signal has a higher frequency in accordance with increasing pixels of image sensors. In addition, in recent years, due to a reduction in a diameter size and an increase in a length of a cable, when a driving signal is transmitted to an image pickup section provided at a distal end portion of an insertion portion, there is a case where the amplitude of the driving signal attenuates and the voltage of the driving signal is below an input lower limit voltage of an image sensor.

Therefore, it can be considered that a cable driver in a processor generates a driving signal having a voltage higher than an input upper limit voltage of an image sensor, to input the generated driving signal to the image sensor through a diameter-reduced and lengthened cable. In this case, the amplitude of the driving signal whose voltage is higher than the input upper limit voltage of the image sensor is attenuated due to transmission through the cable, and therefore the driving signal meets the input voltage standard when the driving signal is inputted to the image sensor.

As described above, in order to output the driving signal that meets the input voltage standard to the image sensor, if the driving signal is generated at a voltage value higher than the input upper limit voltage value with respect to the image sensor in anticipation of the attenuation amount due to the transmission of the driving signal through the cable, the DC voltage to be inputted to the image sensor when the power source of the processor is turned on or off is maintained at a voltage value higher than the input upper limit voltage of the image sensor.

SUMMARY OF THE INVENTION

An endoscope system according to one aspect of the present invention includes: an image pickup section provided with a solid-state image pickup device and configured to obtain an examination image; a cable that transmits the examination image; and a processor that receives the examination image, performs image processing, and displays the processed image, the processor including: a cable driver that applies a voltage higher than an input voltage standard of the image pickup section so as to compensate for attenuation of a high-frequency signal caused by the cable and outputs a clock signal for driving the image pickup section; a first peaking circuit that performs waveform correction of the clock signal; and a first level limiting circuit configured to limit, when the clock signal inputted from the first peaking circuit is switched to a DC voltage, an amplitude level of the DC voltage so as not to exceed a level of the input voltage standard of the image pickup section.

In addition, an endoscope system according to another aspect of the present invention includes: an image pickup section provided with a solid-state image pickup device and configured to obtain an examination image; a cable that transmits the examination image; and a processor that receives the examination image, performs image processing, and displays the processed image, the processor including: a level limiting circuit that detects a clock signal for driving the image pickup section, the level limiting circuit being configured to output the clock signal when the clock signal is detected and output a signal whose output level is limited so as not to exceed a level of an input voltage standard of the image pickup section when the clock signal is not detected; and a peaking circuit that performs waveform correction of the clock signal outputted from the level limiting circuit.

DETAILED DESCRIPTION OF THE PREFERRED EMBODIMENTS

Hereinafter, embodiments of the present invention will be described with reference to drawings.

First Embodiment

Figure 1:
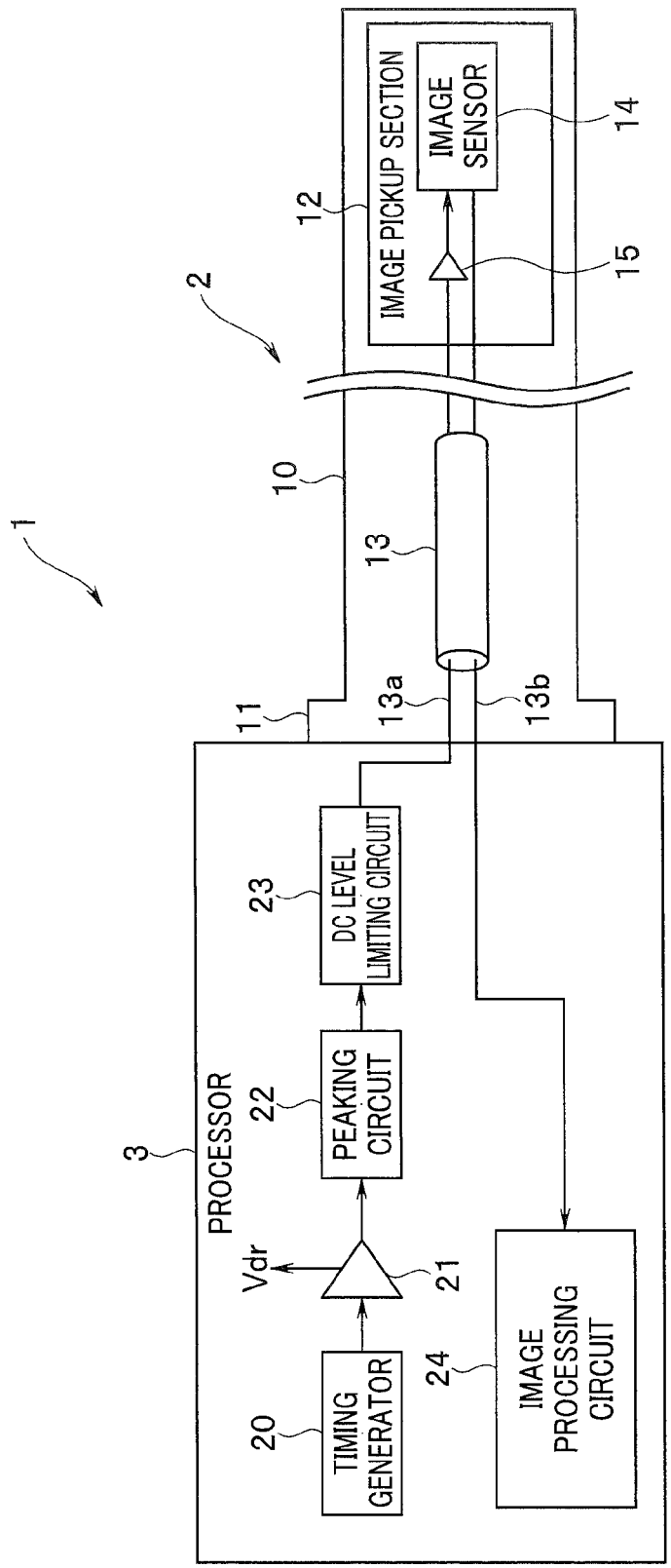
FIG. 1 shows a configuration of an endoscope system according to a first embodiment.
Figure 2:
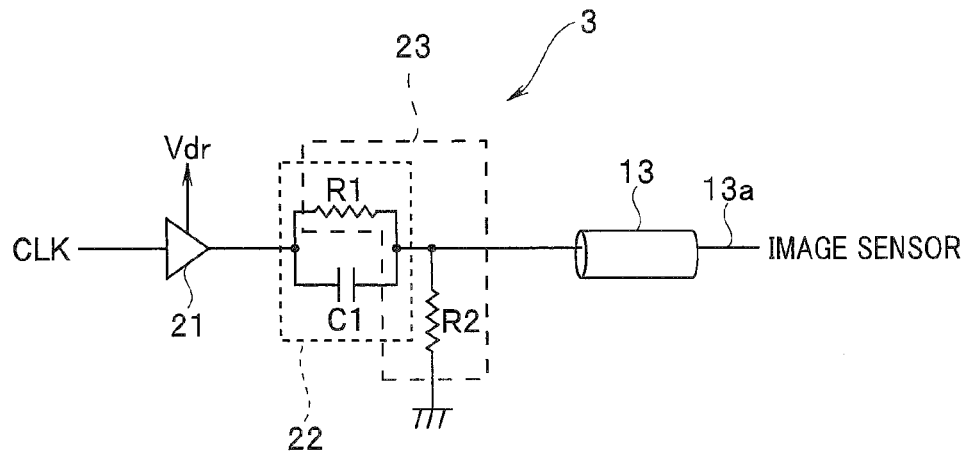
FIG. 2 illustrates a detailed circuit configuration of a processor according to the first embodiment.

First, description will be made on a configuration of an endoscope system according to the first embodiment with reference to FIG. 1 and FIG. 2. FIG. 1 shows the configuration of the endoscope system according to the first embodiment, and FIG. 2 illustrates a detailed circuit configuration of a processor according to the first embodiment.

As shown in FIG. 1, an endoscope system 1 includes an endoscope 2 and a processor 3. The endoscope 2 includes an elongate insertion portion 10 configured to be inserted into a subject to be examined, and a connector portion 11 provided on the proximal end side of the insertion portion 10. The endoscope 2 is configured to be attachable to and detachable from the processor 3 through the connector section 11.

The insertion portion 10 includes at a distal end portion thereof an image pickup section 12. The image pickup section 12 is connected with a cable 13. The image pickup section 12 is provided with an image sensor 14 such as CCD, and a driver 15 that amplifies a driving signal to be supplied to the image sensor 14, for example. A signal line 13a for supplying the driving signal outputted from the processor 3 to the image sensor 14 and a signal line 13b for supplying an image pickup signal obtained by image pickup with the image sensor 14 to the processor 3 are inserted through the cable 13.

The processor 3 includes at least a timing generator 20, a cable driver 21, a peaking circuit 22, a DC level limiting circuit 23, and an image processing circuit 24.

The timing generator 20 outputs a clock signal CLK, which is a driving signal to be supplied to the image sensor 14, to the cable driver 21.

The cable driver 21, in order to compensate for attenuation of a high-frequency signal caused by the cable 13, amplifies the amplitude of the clock signal CLK at a predetermined voltage Vdr higher than an input voltage standard of the image sensor 14, to output the amplified clock signal to the peaking circuit 22.

As shown in FIG. 2, the peaking circuit 22 is configured by a resistor R1 and a capacitor C1 which are connected in parallel, and performs waveform correction processing so as to add a peak portion to an edge portion of the waveform with respect to the clock signal CLK outputted from the cable driver 21, to output the clock signal subjected to the processing to the DC level limiting circuit 23.

As shown in FIG. 2, the DC level limiting circuit 23 is configured by the resistor R1 and a resistor R2 connected in series with the resistance R1, and controls the amplitude level of the inputted signal so as not to exceed the level of the input voltage standard of the image pickup section 12 by a resistor divided voltage obtained through the resistors R1, R2, when the inputted signal is switched to the DC voltage. That is, the DC level limiting circuit 23 allows the clock signal whose voltage is the AC voltage to pass through as it is, and limit (reduce the amplitude of) only the DC voltage generated by ON/OFF of the power source, and the like.

The driving signal outputted from the DC level limiting circuit 23 is supplied to the driver 15 of the image pickup section 12 through the signal line 13a of the cable 13. The driver 15 amplifies the supplied driving signal and supplies the amplified driving signal to the image sensor 14.

The image sensor 14 is driven with the supplied driving signal, and outputs an image pickup signal obtained by picking up an optical image of the subject to be examined to the image processing circuit 24 in the processor 3, through the signal line 13b of the cable 13.

The image processing circuit 24 performs predetermined image processing on the image pickup signal outputted from the image sensor 14, to output the image signal subjected to the predetermined image processing to a monitor or recording device, not shown, and display or record the image.

Hereinafter, the working of the endoscope system 1 thus configured will be described.

Figure 3:
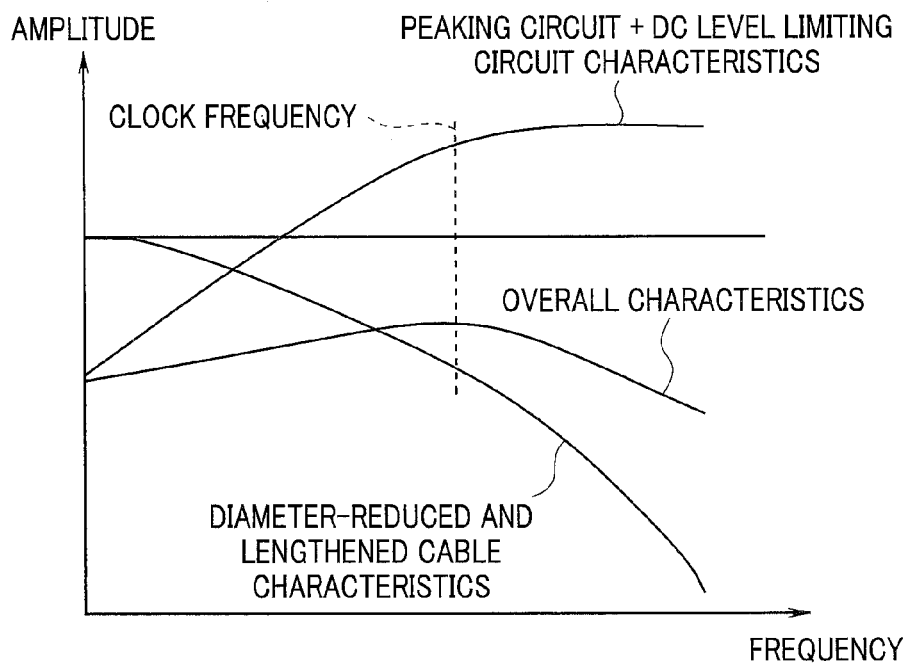
FIG. 3 shows frequency characteristics of a cable 13, a peaking circuit 22, and a DC level limiting circuit 23.
Figure 4A:
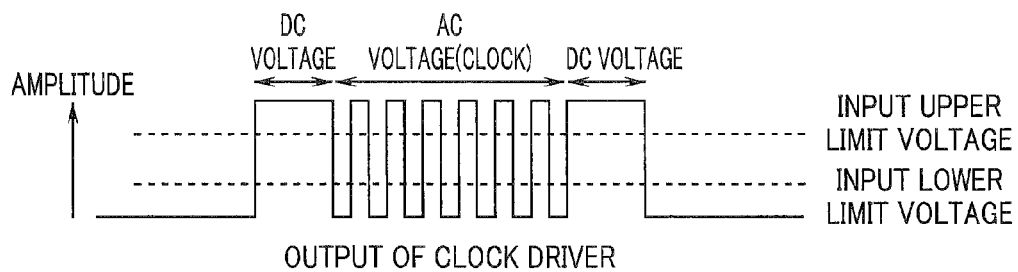
FIG. 4A shows a timing chart of a clock signal CLK in each circuit section.
Figure 4B:
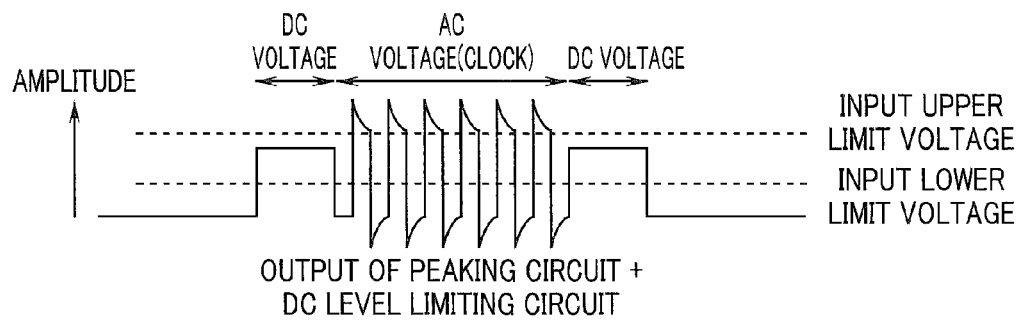
FIG. 4B shows a timing chart of the clock signal CLK in each circuit section.
Figure 4C:
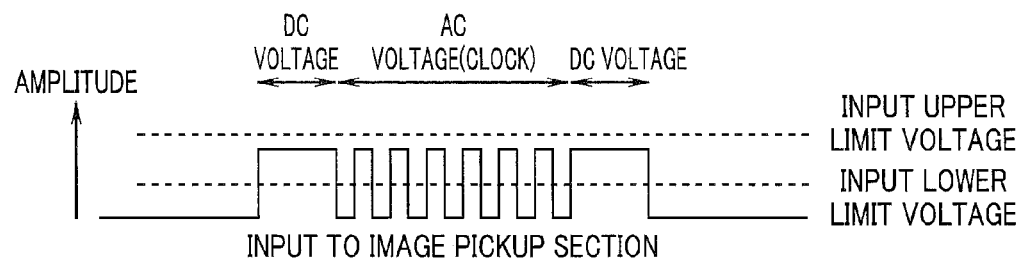
FIG. 4C shows a timing chart of the clock signal CLK in each circuit section.

FIG. 3 illustrates frequency characteristics of the cable 13, the peaking circuit 22 and the DC level limiting circuit 23, and each of FIGS. 4A to 4C illustrates a timing chart of the clock signal CLK in each of the circuit sections.

As shown in FIG. 3, the diameter-reduced and lengthened cable 13 has frequency characteristics in which the amplitude decreases as the frequency of the signal becomes higher. The peaking circuit 22 and the DC level limiting circuit 23 have frequency characteristics in which the amplitude has a peak around the frequency of the clock signal CLK. Thus, the cable 13, peaking circuit 22 and DC level limiting circuit 23 have overall characteristics in which the amplitude has a peak around the frequency of the clock signal CLK.

The cable driver 21 amplifies the inputted signal at a predetermined voltage Vdr, i.e., a voltage exceeding the input voltage standard of the image sensor 14 in the present embodiment. As shown in FIG. 4A, the signal whose amplitude is amplified to an amplitude exceeding the input upper limit voltage of the image pickup section 12 is outputted from the cable driver 21, to be inputted to the peaking circuit 22.

The peaking circuit 22 performs waveform correction so as to add a peak portion to an edge portion of the clock signal CLK. In addition, the DC level limiting circuit 23 limits the level of the signal components of the DC voltage whose frequency is slow by the resistor divided voltage obtained through the resistor R1 and the resistor R2 connected in series with the resistor R1 so as not to exceed the level of the input upper limit voltage of the image pickup section 12. As a result, the signal having the waveform shown in FIG. 4B is outputted from the peaking circuit 22 and the DC level limiting circuit 23.

The signal having the waveform as shown in FIG. 4B is inputted to the image pickup section 12 as a result that the amplitude of the clock signal CLK whose frequency is high is attenuated to fall within between the input upper limit voltage and the input lower limit voltage of the image pickup section 12 due to the cable characteristics of the diameter-reduced and lengthened cable 13, as shown in FIG. 4C. At this time, the DC voltage whose frequency is low is little affected by the amplitude attenuation caused by the cable 13, and inputted to the image pickup section 12. Therefore, even if the driving signal is amplified by the cable driver 21 to a voltage higher than the input upper limit voltage of the image pickup section 12, the signal inputted to the image pickup section 12 falls within between the input upper limit voltage and the input lower limit voltage, as shown in FIG. 4C. As a result, the driving signal meets the input voltage standard of the image sensor 14.

As described above, according to the endoscope system 1 of the present embodiment, even in the case where the clock signal CLK whose voltage is increased by using the voltage exceeding the input voltage standard of the image sensor 14 is inputted to the cable driver 21, the amplitude is attenuated with the diameter-reduced and lengthened cable 13. Therefore, the clock signal CLK that meets the input voltage standard is inputted to the image sensor 14. In addition, the endoscope system 1 is configured to meet the input voltage standard of the image sensor 14 by attenuating the low frequency DC voltage by the DC level limiting circuit 23 even in the case where the DC voltage is generated at the time of ON/OFF of the power source when the driving voltage exceeding the input voltage standard of the image sensor 14 is used for the cable driver 21.

Therefore, the endoscope system according to the present embodiment enables the signal having the voltage that meets the input voltage standard to be inputted to the image sensor.

Modified Example

Next, a modified example of the first embodiment will be described.

Figure 5:
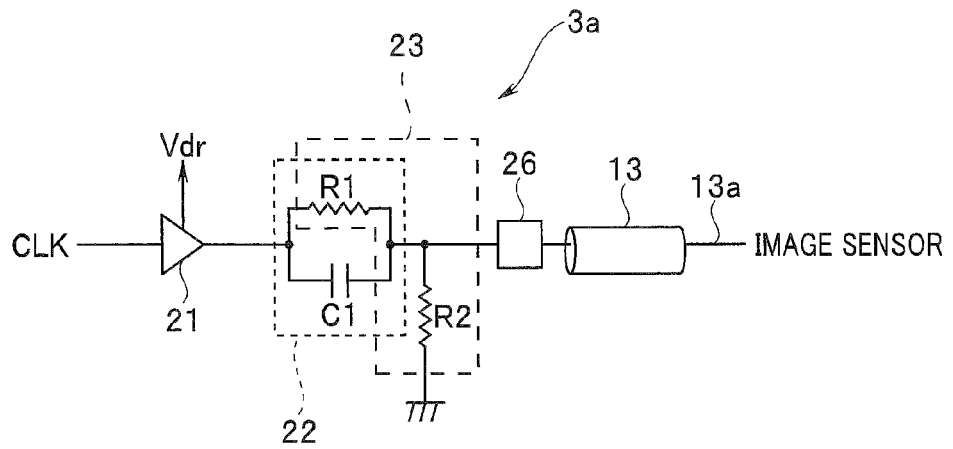
FIG. 5 illustrates a detailed circuit configuration of a processor according to a modified example of the first embodiment.

FIG. 5 illustrates a detailed circuit configuration of a processor according to the modified example of the first embodiment. Note that the components in FIG. 5 which are the same as those in FIG. 2 are attached with the same reference numerals and descriptions thereof will be omitted.

As shown in FIG. 5, a processor 3a according to the modified example of the first embodiment is configured by adding, to the processor 3 according to the first embodiment, a noise filter 26 for eliminating high-frequency noise arranged at the output stage of the DC level limiting circuit 23. The noise filter 26 eliminates the high-frequency noise of the clock signal CLK outputted from the DC level limiting circuit 23 and outputs the clock signal CLK from which the high-frequency noise has been eliminated to the image sensor 14 of the image pickup section 12 through the cable 13.

In the above-described first embodiment, the voltage exceeding the input voltage standard of the image sensor 14 can be used for the cable driver 21, thereby capable of increasing the amplitude of the clock signal CLK transmitted through the cable 13. By taking advantage of the increased amplitude, the processor 3a eliminates the high-frequency noise by arranging the noise filter 26 at the output stage of the DC level limiting circuit 23.

According to such a configuration, the processor 3a of the present modified example is capable of suppressing unnecessary high-frequency components, though the amplitude of the signal clock CLK and rise time and fall time of the waveform of the clock signal CLK are sacrificed in some degree. Therefore, it is possible to strengthen EMC (Electro-Magnetic Compatibility) more than in the above-described embodiment.

Second Embodiment

Figure 6:
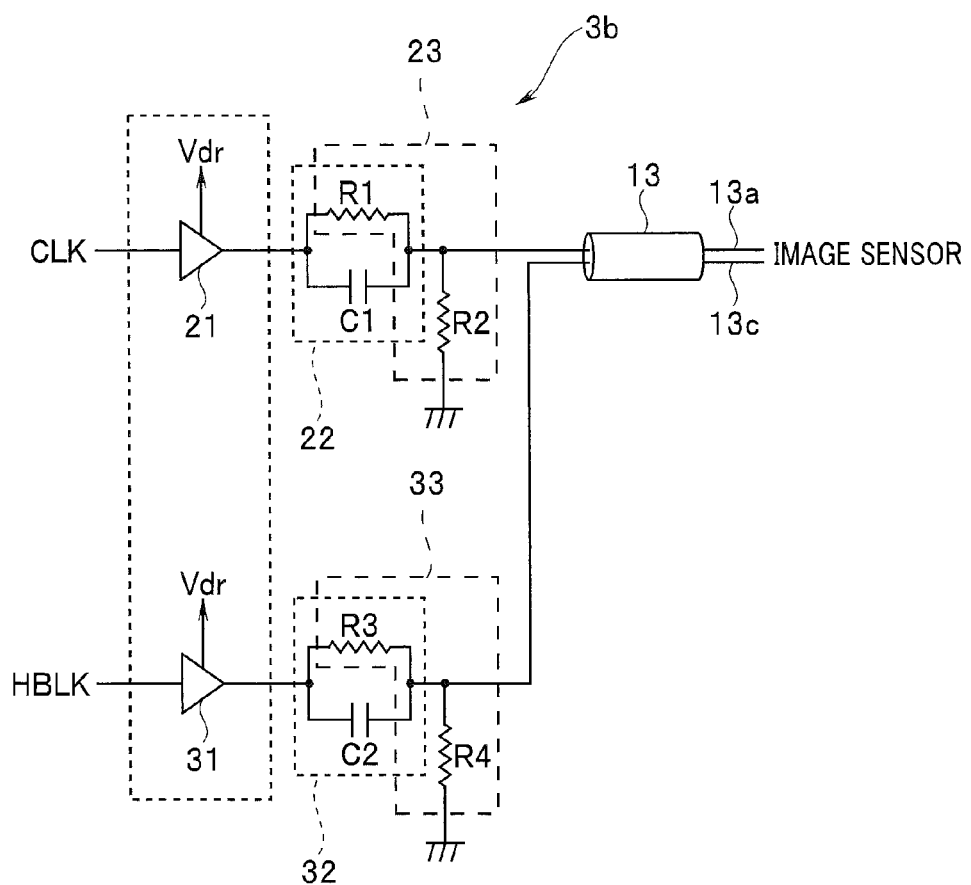
FIG. 6 illustrates a detailed circuit configuration of a processor according to a second embodiment.

Next, the second embodiment will be described. FIG. 6 illustrates a detailed circuit configuration of a processor according to the second embodiment. Note that the components in FIG. 6 which are the same as those in FIG. 2 are attached with the same reference numerals and descriptions thereof will be omitted.

As shown in FIG. 6, a processor 3b according to the present embodiment is configured by adding a cable driver 31, a peaking circuit 32, a DC level limiting circuit 33, and a signal line 13c to the processor 3 according to the first embodiment. A horizontal synchronization signal HBLK to be supplied to the image pickup section 12 is transmitted through the cable driver 31, the peaking circuit 32, the DC level limiting circuit 33, and the signal line 13c.

The horizontal synchronization signal HBLK is inputted to the cable driver 31. The horizontal synchronization signal HBLK is, due to the low frequency thereof, little affected by the amplitude attenuation caused by the cable 13. Therefore, it is not necessary to use a voltage higher than the input voltage standard of the image sensor 14 for the cable driver 31. However, there is a case where the image pickup section 12 specifies the input phase standard showing a relation between the clock signal CLK and the horizontal synchronization signal HBLK.

In that case, if different cable drivers are used for the clock signal CLK and the horizontal synchronization signal HBLK, the signals are affected by variation in signal delay due to the difference of the drivers, which cause a difficulty in meeting the input phase standard showing the relation between the clock signal CLK and the horizontal synchronization signal HBLK.

In order to suppress the variation in the signal delays of the clock signal CLK and the horizontal synchronization signal HBLK, it is desirable to use equivalent cable drivers for the clock signal CLK and the horizontal synchronization signal HBLK. In the present embodiment, the cable driver 31 which is equivalent to the cable driver 21 for the clock signal CLK is arranged on the transmission path of the horizontal synchronization signal HBLK. That is, the cable driver 31 amplifies the amplitude of the horizontal synchronization signal HBLK at a predetermined voltage Vdr higher than the input voltage standard of the image sensor 14, to output the amplified horizontal synchronization signal HBLK to the peaking circuit 32.

As described above, since the horizontal synchronization signal HBLK has low frequency and the amplitude thereof is hardly attenuated by the cable 13, if the predetermined voltage Vdr higher than the input voltage standard of the image sensor 14 is used for the cable driver 31, the horizontal synchronization signal HBLK fails to meet the input voltage standard of the image sensor 14.

Therefore, the peaking circuit 32 and the DC level limiting circuit 33 are configured by using a resistor R3, a capacitor C2, and a resistor R4 so as to have frequency characteristics different from the frequency characteristics of the peaking circuit 22 and the DC level limiting circuit 23 provided on the path of the clock signal CLK.

In the present embodiment, the peaking circuit 32 is configured by the resistor R3 and the capacitor C2 different from the resistor R1 and the capacitor C1 of the peaking circuit 22. In addition, the DC level limiting circuit 33 is configured by the resistors R3, R4 different from the resistors R1, R2 of the DC level limiting circuit 23.

The peaking circuit 32 performs waveform correction processing so as to add a peak portion to an edge portion of the waveform with respect to the horizontal synchronization signal HBLK from the cable driver 31, and outputs the clock signal subjected to the waveform correction processing to the DC level limiting circuit 33.

The DC level limiting circuit 33 limits the level (reduces the amplitude) of the horizontal synchronization signal HBLK whose voltage is the DC voltage, and outputs the resultant horizontal synchronization signal to the image sensor 14 of the image pickup section 12 through the signal line 13c inserted through the cable 13.

Next, the operation of the endoscope system 1 thus configured will be described.

Figure 7:
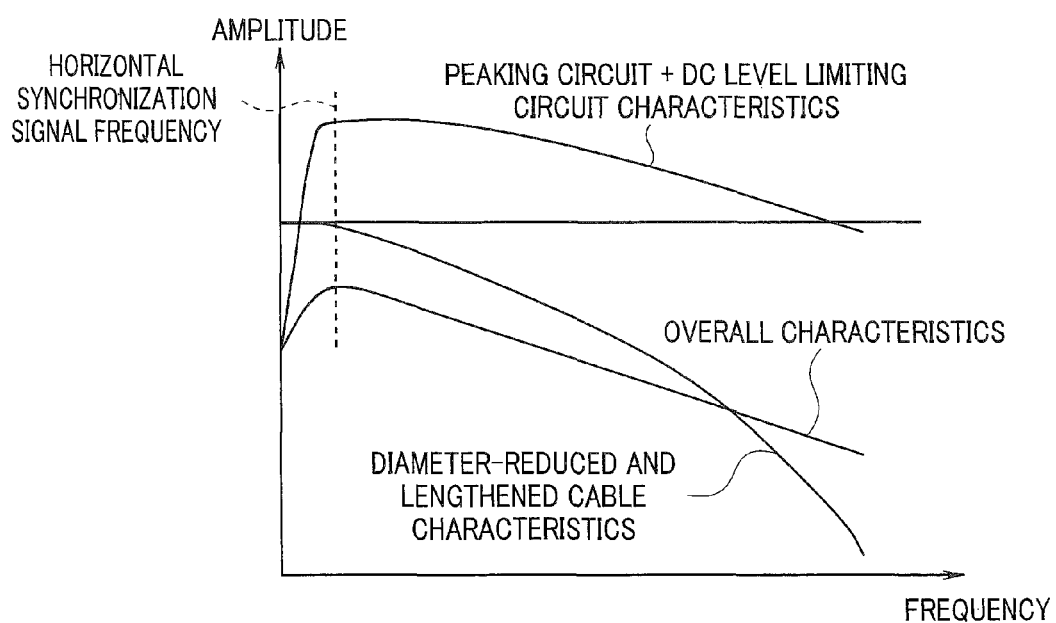
FIG. 7 shows frequency characteristics of the cable 13, a peaking circuit 32, and a DC level limiting circuit 33.
Figure 8A:
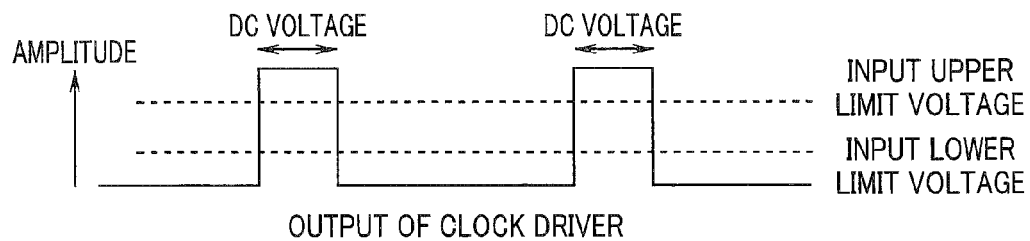
FIG. 8A shows a timing chart of a horizontal synchronization signal HBLK in each circuit section.
Figure 8B:
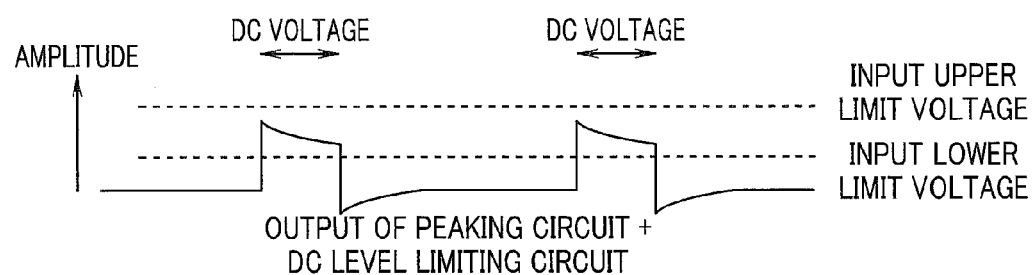
FIG. 8B shows a timing chart of the horizontal synchronization signal HBLK in each circuit section.
Figure 8C:
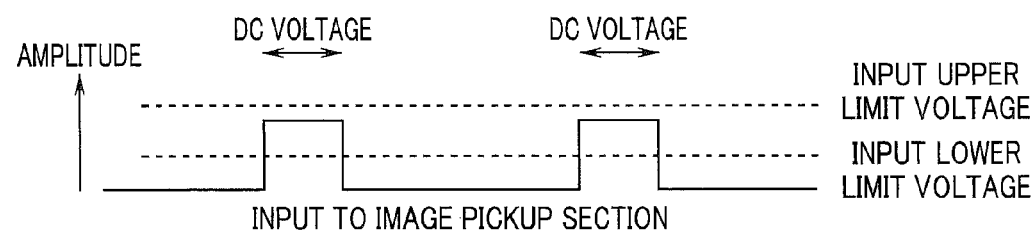
FIG. 8C shows a timing chart of the horizontal synchronization signal HBLK in each circuit section.

FIG. 7 illustrates frequency characteristics of the cable 13, the peaking circuit 32 and the DC level limiting circuit 33, and each of FIGS. 8A to 8C illustrates a timing chart of the horizontal synchronization signal HBLK in each of the circuit sections.

As shown in FIG. 7, the diameter-reduced and lengthened cable 13 is configured to have frequency characteristics in which the amplitude decreases as the frequency of the signal becomes higher. The peaking circuit 32 and the DC level limiting circuit 33 have frequency characteristics in which the amplitude has a peak around the frequency of the horizontal synchronization signal HBLK. That is, the cable 13, peaking circuit 32 and DC level limiting circuit 33 have overall characteristics in which the amplitude has a peak around the frequency of the horizontal synchronization signal HBLK.

The cable driver 31 amplifies the inputted signal at the predetermined voltage Vdr, i.e., the voltage exceeding the input voltage standard of the image sensor 14 in the present embodiment. As shown in FIG. 8A, the signal whose amplitude is amplified to the amplitude exceeding the input upper limit voltage of the image pickup section 12 is outputted from the cable driver 31, to be inputted to the peaking circuit 32.

The peaking circuit 32 performs waveform correction so as to add the peak portion to the edge portion of the horizontal synchronization signal HBLK. In addition, the DC level limiting circuit 33 limits the level of the signal components of the DC voltage whose frequency is slow by the resistor divided voltage obtained through the resistor R3 and the resistor R4 so as not to exceed the level of the input upper limit voltage of the image pickup section 12. As a result, the horizontal synchronization signal HBLK having the waveform shown in FIG. 8B is outputted from the peaking circuit 32 and the DC level limiting circuit 33.

The horizontal synchronization signal HBLK having the waveform shown in FIG. 8B is little affected by the amplitude attenuation caused by the cable 13, and the horizontal synchronization signal HBLK that meets the input voltage standard of the image sensor 14 is inputted to the image pickup section 12, as shown in FIG. 8C.

As described above, the processor 3b according to the present embodiment includes the cable driver 31 equivalent to the one for the clock signal CLK, on the transmission path of the horizontal synchronization signal HBLK and includes the peaking circuit 32 and the DC level limiting circuit 33 that have frequency characteristics different from those of the circuits on the transmission path of the clock signal CLK. Thus, the processor 3b is capable of meeting the input voltage standard of the image sensor 14, and also meeting the input phase standard at the same time.

Third Embodiment

Next, description will be made on the third embodiment.

Figure 9:
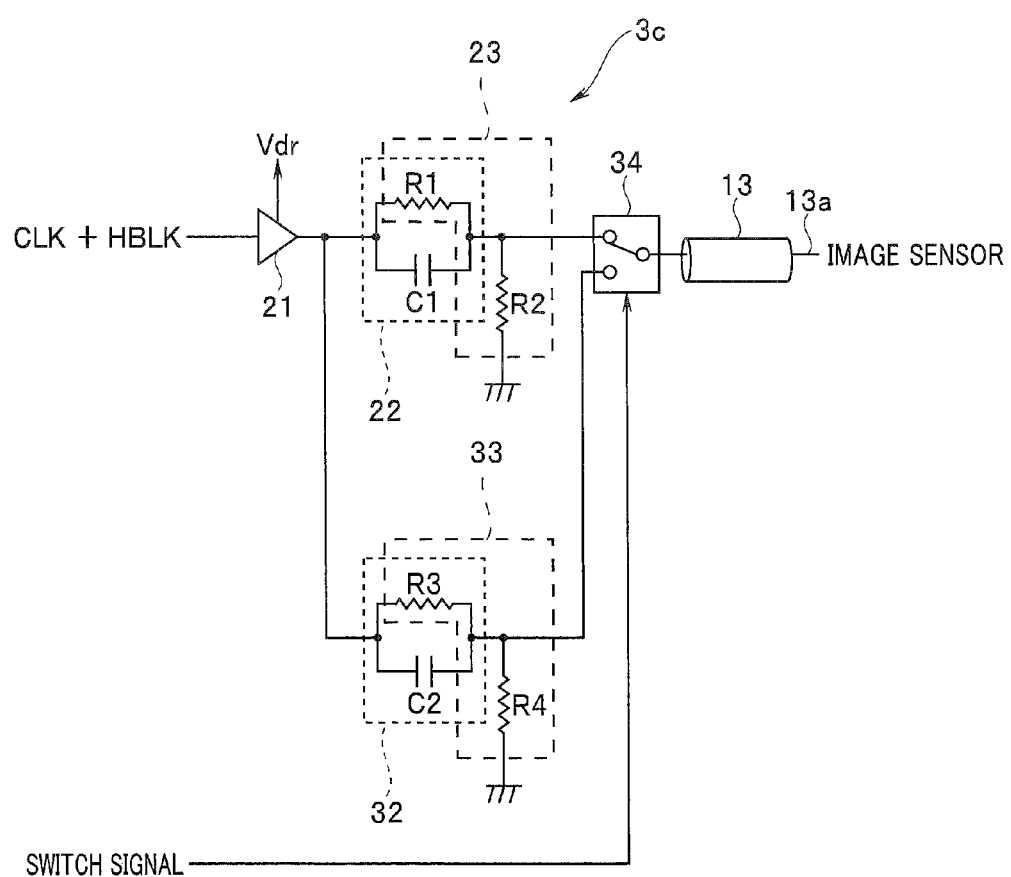
FIG. 9 illustrates a detailed circuit configuration of a processor according to a third embodiment.

FIG. 9 illustrates a detailed circuit configuration of a processor according to the third embodiment. Note that the components in FIG. 9 which are the same as those in FIG. 6 are attached with the same reference numerals and descriptions thereof will be omitted.

For the purpose of reducing the number of signal lines inserted through the cable 13 to reduce the diameter of the insertion portion 10 of the endoscope 2, there is a case where the horizontal synchronization signal HBLK is superimposed on the clock signal CLK as the driving signal for the image sensor 14. Also in this case, there is a desire for increasing the voltage of the cable driver for transmitting the components of the high frequency clock signal CLK. However, the voltage of the low frequency horizontal synchronization signal HBLK becomes large, which problematically results in a failure to meet the input voltage standard of the image sensor 14.

In view of the above, in the third embodiment, description will be made on a processor capable of meeting the input voltage standard of the image sensor 14 even if the horizontal synchronization signal HBLK is superimposed on the clock signal CLK.

As shown in FIG. 9, the processor 3c is configured by removing the cable driver 31 and the signal line 13c from the processor 3b in FIG. 6 and adding a switching section 34 to the processor 3b.

A driving signal obtained by superimposing the horizontal synchronization signal HBLK on the clock signal CLK is inputted to the cable driver 21. The cable driver 21 amplifies the inputted driving signal at a predetermined voltage, to output the amplified driving signal to the peaking circuit 22 and the peaking circuit 32.

The peaking circuit 22 and the DC level limiting circuit 23 correct the edge of the clock signal CLK included in the driving signal, to output the signal shown in FIG. 4B to the switching section 34. On the other hand, the peaking circuit 32 and the DC level limiting circuit 33 correct the edge and limit the level of the horizontal synchronization signal HBLK included in the driving signal and output the signal shown in FIG. 8B to the switching section 34.

When transmitting the clock signal CLK, the switching section 34 selects the driving signal outputted from the peaking circuit 22 and the DC level limiting circuit 23 based on a switch signal, and outputs the selected driving signal to the image sensor 14 through the signal line 13a of the cable 13. On the other hand, when transmitting the horizontal synchronization signal HBLK, the switching section 34 selects the driving signal outputted from the peaking circuit 32 and the DC level limiting circuit 33 based on a switch signal, and outputs the selected driving signal to the image sensor 14 through the signal line 13a of the cable 13.

As described above, the processor 3c is configured to output the signal by selecting the output of the peaking circuit 22 and the level limiting circuit 23 by the switching section 34 when transmitting the clock signal CLK, and selecting the output of the peaking circuit 32 and the DC level limiting circuit 33 by the switching section 34 when transmitting the horizontal synchronization signal HBLK. As a result, the processor 3c according to the present embodiment is capable of reducing the number of signal lines inserted through the cable 13, compared with the processor 3b in the second embodiment, thereby enabling the diameter of the insertion portion 10 to be more reduced than in the processor 3b.

Fourth Embodiment

Next, description will be made on the fourth embodiment.

Figure 10:
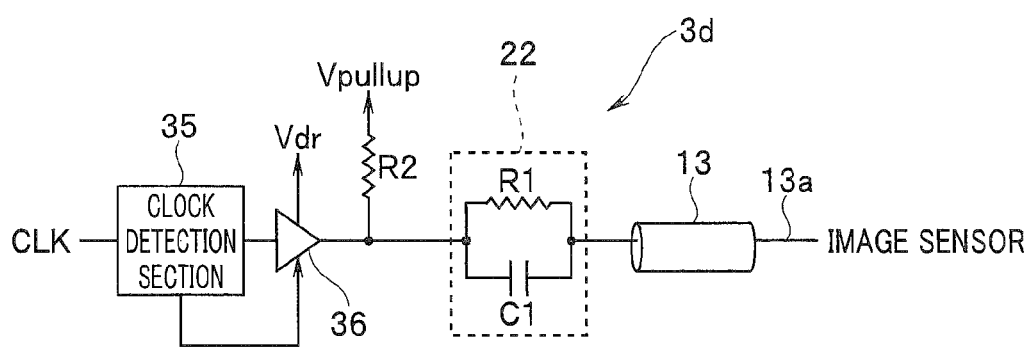
FIG. 10 illustrates a detailed circuit configuration of a processor according to a fourth embodiment.

FIG. 10 illustrates a detailed circuit configuration of a processor according to the fourth embodiment. Note that the components in FIG. 10 which are the same as those in FIG. 2 are attached with the same reference numerals and descriptions thereof will be omitted.

In the second embodiment, a measure for meeting the input voltage standard of the image sensor 14 is taken by the resistor divided voltage. However, if the driving voltage of the cable driver 21 is further increased, there is a case where the input voltage cannot be sufficiently narrowed down even if the voltage is divided by the resistors, which may result in a failure to meet the input voltage standard of the image sensor 14.

In the present embodiment, the processor 3d includes a clock detection section 35 that detects a clock signal CLK, a cable driver 36 that changes the output according to the detection result of the clock detection section 35. The clock detection section 35 detects whether or not the clock signal CLK is inputted, and according to the detection result, outputs a control signal for changing the output of the cable driver 21 to the cable driver 36. In the method of detecting the clock signal CLK, for example, when the inputted clock signal CLK and the delayed and inverted clock signal CLK have the same signal levels ((H, H) or (L, L)), it is determined that the clock signal CLK has been inputted.

That is, when the clock signal CLK is detected by the clock detection section 35, the cable driver 36 outputs the clock signal CLK. On the other hand, when the clock signal CLK is not detected by the clock detection section 35, the cable driver 36 outputs Hi-Z. The signal level in the output of the cable driver 36 becomes Vpullup through the pullup resistor R2 and then the signal is inputted to the peaking circuit 22.

Thus, if the driving signal is not the clock signal CLK, that is, the voltage of the inputted signal is the DC voltage, the clock detection section 35 and the cable driver 36 configure a DC level limiting circuit that limits the level of the DC voltage.

Figure 11:
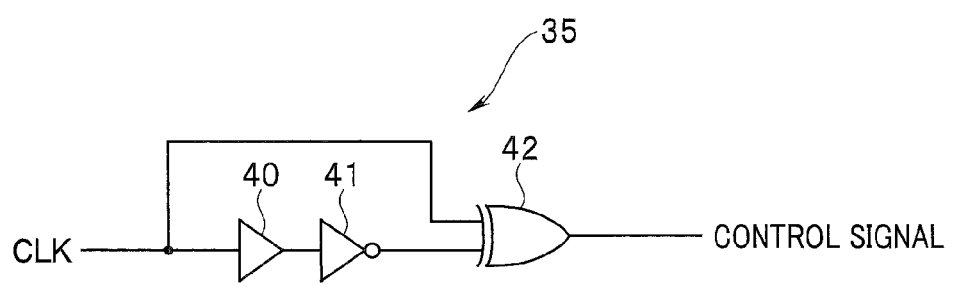
FIG. 11 illustrates a detailed circuit configuration of a clock detection section 35.

FIG. 11 illustrates a detailed circuit configuration of the clock detection section 35. As shown in FIG. 11, the clock detection section 35 includes: a delay circuit 40 configured by a buffer, for example; an inverting circuit 41 configured by an inverter, for example; and an XOR circuit 42.

The clock signal CLK is inputted to the delay circuit 40. The delay circuit 40 delays the inputted clock signal CLK by a predetermined time period, and outputs the delayed clock signal to the inverting circuit 41. The inverting circuit 41 inverts the clock signal CLK delayed by the delay circuit 40, to output the inverted clock signal to the XOR circuit 42.

The clock signal CLK is inputted to one of the input terminals of the XOR circuit 42, and the clock signal CLK delayed by the delay circuit 40 and inverted by the inverting circuit 41 is inputted to the other of the input terminals of the XOR circuit 42. The XOR circuit 42 performs XOR operation of the inputted clock signal CLK and the clock signal CLK delayed by the delay circuit 40 and inverted by the inverting circuit 41, and outputs the operation result to the cable driver 36 as a control signal. That is, when the inputted clock signal CLK and the delayed and inverted clock signal CLK have the same signal levels ((H, H) or (L, L)), the XOR circuit 42 outputs an L-level signal to the cable driver 36 as the control signal. On the other hand, when the inputted clock signal CLK and the delayed and inverted clock signal CLK have different signal levels ((H, L) or (L, H)), the XOR circuit 42 outputs an H-level signal to the cable driver 36 as the control signal.

When the control signal is the L-level signal, the cable driver 36 amplifies the clock signal CLK at a predetermined voltage and outputs the amplified clock signal to the peaking circuit 22. On the other hand, when the control signal is the H-level signal, the cable driver 36 stops the output of the clock signal CLK and outputs Hi-Z.

Next, the operation of the endoscope system 1 thus configured will be described.

Figure 12A:
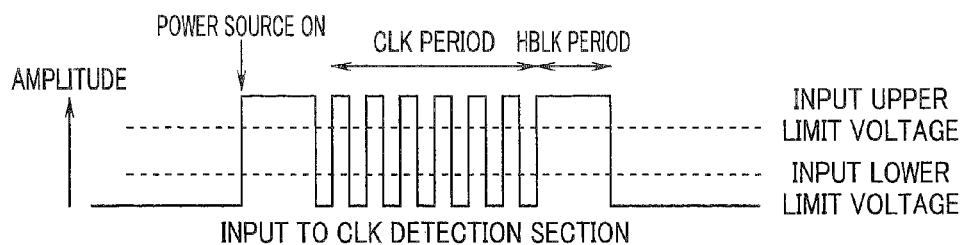
FIG. 12A shows a timing chart of a driving signal in each circuit section.
Figure 12B:
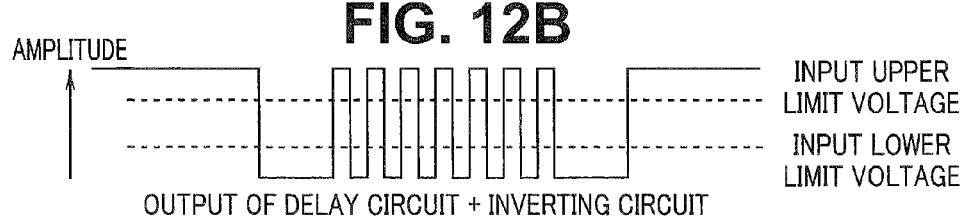
FIG. 12B shows a timing chart of the driving signal in each circuit section.
Figure 12C:
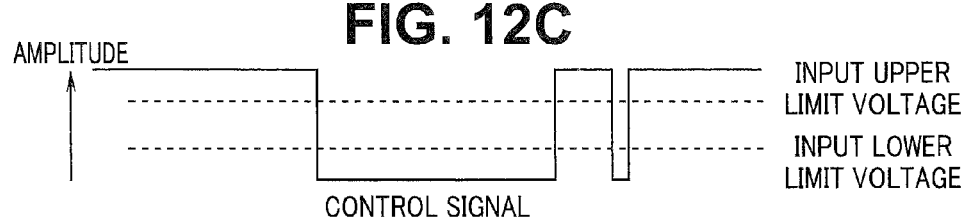
FIG. 12C shows a timing chart of the driving signal in each circuit section.

Each of FIGS. 12A to 12F illustrates a timing chart of the driving signal in each of the circuit sections. As shown in FIG. 12A, the DC voltage generated when the power source is turned on and signals such as the clock signal CLK and the horizontal synchronization signal HBLK are inputted to the clock detection section 35. As shown in FIG. 12B, the signal obtained by delaying the inputted signal by one-half cycle of the clock signal CLK and inverting the delayed clock signal is outputted from the delay circuit 40 and the inverting circuit 41 of the clock detection section 35. The clock signal CLK inputted to the clock detection section 35 and the clock signal CLK delayed by the delay circuit 40 and inverted by the inverting circuit 41 are subjected to an EOR operation by the XOR circuit 42, and outputted to the cable driver 36 as the control signal, as shown in FIG. 12C.

Figure 12D:
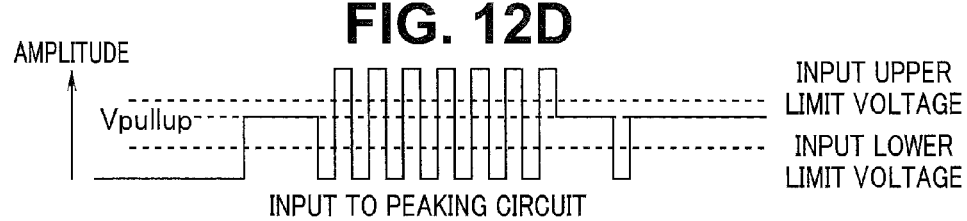
FIG. 12D shows a timing chart of the driving signal in each circuit section.
Figure 12E:
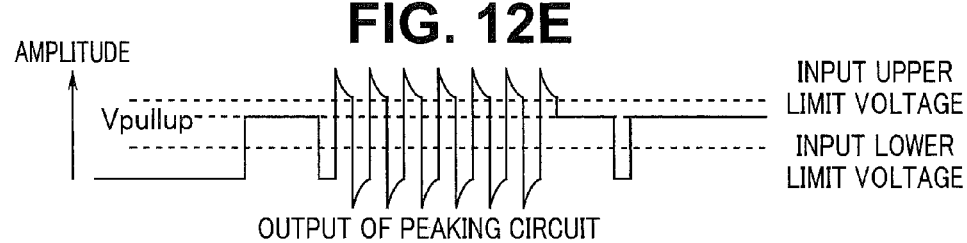
FIG. 12E shows a timing chart of the driving signal in each circuit section.

The cable driver 36 outputs Hi-Z when the control signal is the H-level signal, and outputs the clock signal CLK when the control signal is the L-level signal, to thereby allow the signal having the waveform as shown in FIG. 12D to be inputted to the peaking circuit 22. The peaking circuit 22 performs waveform correction so as to add the peak portion to the edge portion of the waveform with respect to the inputted clock signal CLK, as shown in FIG. 12E, and outputs the clock signal CLK subjected to the waveform correction to the cable 13.

Figure 12F:
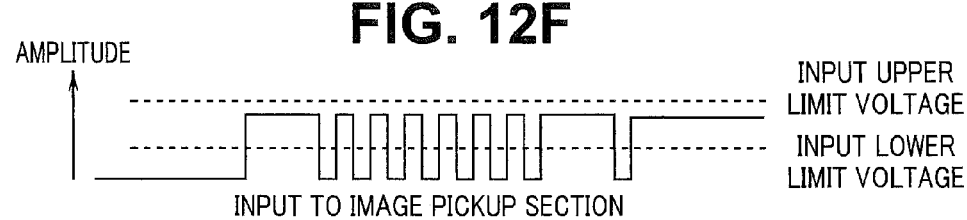
FIG. 12F shows a timing chart of the driving signal in each circuit section.

In the output of the peaking circuit 22, the amplitude of the clock signal CLK whose frequency is high is attenuated by the diameter-reduced and lengthened cable 13. On the other hand, the horizontal synchronization signal HBLK whose frequency is low is little affected by the amplitude attenuation caused by the cable 13. Therefore, as shown in FIG. 12F, the driving signal that meets the input voltage standard is inputted to the image sensor 14 of the image pickup section 12.

As described above, the processor 3d of the present embodiment is configured to set the output of the cable driver 36 to Hi-Z when the clock detection section 35 detects the clock signal CLK, to enable the input voltage standard of the image sensor 14 to be met, even if the driving voltage of the cable driver 36 is increased more than in the first embodiment.

Modified Example

Figure 13:
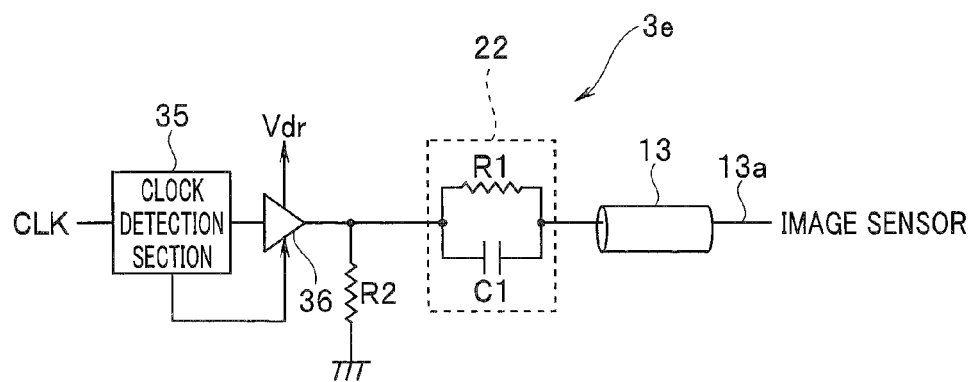
FIG. 13 illustrates a detailed circuit configuration of a processor according to a modified example of the fourth embodiment.

Next, a modified example of the fourth embodiment will be described. FIG. 13 illustrates a detailed circuit configuration of a processor according to the modified example of the fourth embodiment. Note that the components in FIG. 13 which are the same as those in FIG. 10 are attached with the same reference numerals and descriptions thereof will be omitted.

As shown in FIG. 13, a processor 3e according to the modified example is configured by using a pulldown resistor R2 instead of the pullup resistor R2 in FIG. 11. In the above-described fourth embodiment, it is supposed that the horizontal synchronization signal HBLK is the H-level signal. However, there is a case where the horizontal synchronization signal HBLK is the L-level signal.

When the clock signal CLK is not detected by the clock detection section 35, the output of the cable driver 36 is set to Hi-Z. The output of the cable driver 36 is inputted to the peaking circuit 22 after the signal level is brought into the L-level by the pulldown resistor R2.

Figure 14A:
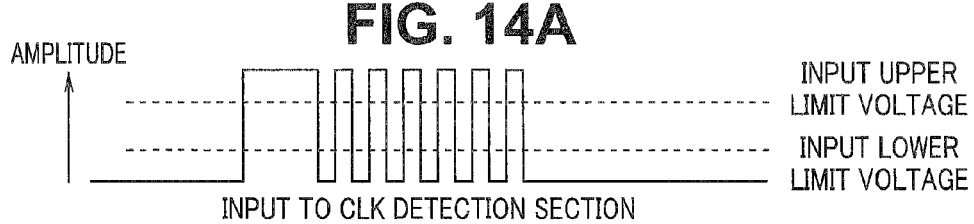
FIG. 14A shows a timing chart of the driving signal in each circuit section.
Figure 14B:
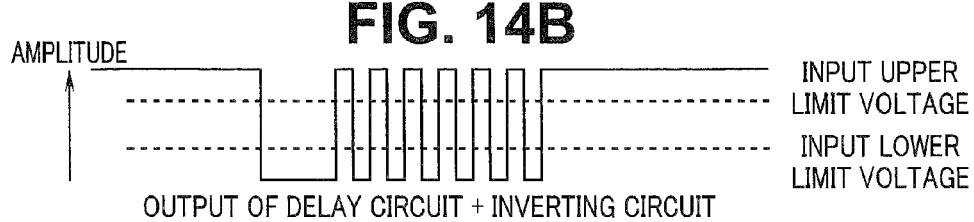
FIG. 14B shows a timing chart of the driving signal in each circuit section.
Figure 14C:
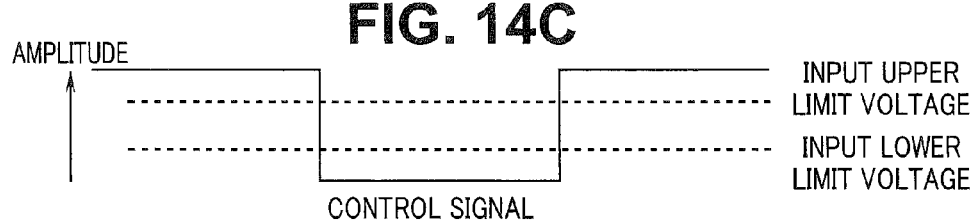
FIG. 14C shows a timing chart of the driving signal in each circuit section.

Each of FIGS. 14A to 14F illustrates a timing chart of the driving signal in each of the circuit sections. As shown in FIG. 14A, the DC voltage generated at the time when the power source is turned on, and signals such as the clock signal CLK, the horizontal synchronization signal HBLK, and the like are inputted to the clock detection section 35. The delay circuit 40 and the inverting circuit 41 in the clock detection section 35 output the signal obtained by delaying the inputted signal by one-half cycle of the clock signal CLK and inverting the delayed signal, as shown in FIG. 14B. The clock signal CLK inputted to the clock detection section 35 and the clock signal CLK delayed by the delay circuit 40 and inverted by the inverting circuit 41 are subjected to the EOR operation in the XOR circuit 42 and the resultant signal is outputted as a control signal to the cable driver 36, as shown in FIG. 14C.

Figure 14D:
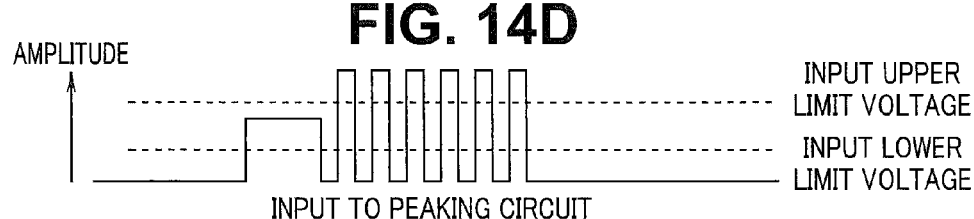
FIG. 14D shows a timing chart of the driving signal in each circuit section.
Figure 14E:
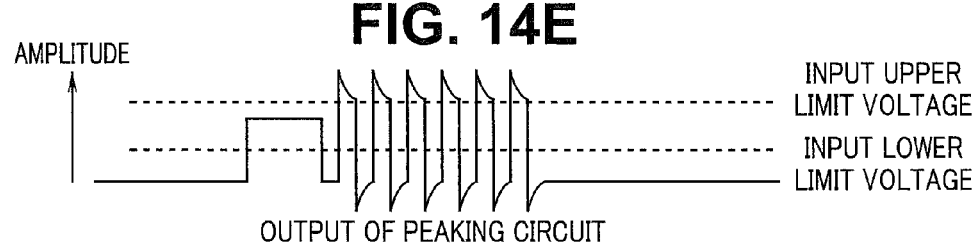
FIG. 14E shows a timing chart of the driving signal in each circuit section.

The cable driver 36 outputs Hi-Z when the control signal is the H-level signal, and outputs the clock signal CLK when the control signal is the L-level signal, which allows the signal of the waveform shown in FIG. 14D to be inputted to the peaking circuit 22. As shown in FIG. 14E, the peaking circuit 22 performs the waveform correction so as to add the peak portion to the edge portion of the waveform with respect to the inputted clock signal CLK, and outputs the signal subjected to the waveform correction to the cable 13.

Figure 14F:
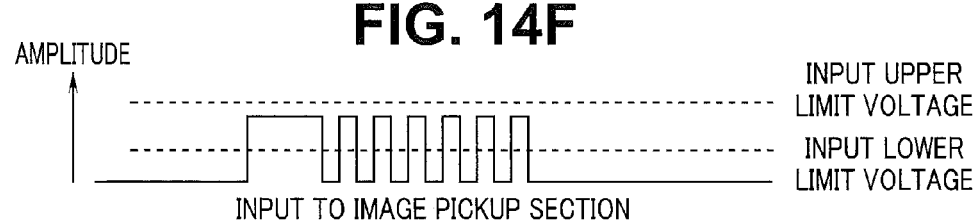
FIG. 14F shows a timing chart of the driving signal in each circuit section.

In the output of the peaking circuit 22, the amplitude of the clock signal CLK whose frequency is high is attenuated by the diameter-reduced and lengthened cable 13. As a result, as shown in FIG. 14F, the driving signal that meets the input voltage standard is inputted to the image sensor 14 of the image pickup section 12.

With such a processor 3e according to the modified example, similarly as in the fourth embodiment, even if the driving voltage of the cable driver 36 is increased more than in the first embodiment, the input voltage standard of the image sensor 14 can be met.

The present invention is not limited to the above-described embodiments and various changes, modifications, and the like are possible in a range without changing the gist of the present invention.

What is claimed is:

1. An endoscope system comprising: an image pickup section provided with a solid-state image pickup device and configured to obtain an examination image; a cable that transmits the examination image; and a processor that receives the examination image, performs image processing, and displays the processed image, the processor comprising:
a cable driver that applies a voltage higher than an input voltage standard of the image pickup section so as to compensate for attenuation of a high-frequency signal caused by the cable and outputs a clock signal for driving the image pickup section;
a first peaking circuit that performs waveform correction of the clock signal; and
a first level limiting circuit configured to limit, when the clock signal inputted from the first peaking circuit is switched to a DC voltage, an amplitude level of the DC voltage so as not to exceed a level of the input voltage standard of the image pickup section.

2. The endoscope system according to claim 1, wherein the first peaking circuit is configured by a first resistor and a first capacitor that are connected in parallel, and
the first level limiting circuit is configured by the first resistor and a second resistor connected in series with the first resistor, and when the clock signal is switched to the DC voltage, outputs a resistor divided voltage obtained through the first resistor and the second resistor to the image pickup section.

3. The endoscope system according to claim 1, further comprising, on a transmission path of a horizontal synchronization signal other than a transmission path of the clock signal, a second peaking circuit that performs waveform correction of the horizontal synchronization signal and a second level limiting circuit that limits an amplitude level of the horizontal synchronization signal so as not to exceed the level of the input voltage standard of the image pickup section.

4. The endoscope system according to claim 3, wherein
a superimposed signal obtained by superimposing the horizontal synchronization signal on the clock signal is inputted to the cable driver, and
the endoscope system further includes a switching section that performs switching to select an output of the first level limiting circuit in a period while the clock signal is inputted and select an output of the second level limiting circuit in a period while the horizontal synchronization signal is inputted, based on a switch signal.

5. The endoscope system according to claim 3, wherein
the second peaking circuit is configured by a third resistor and a second capacitor that are connected in parallel, and
the second level limiting circuit is configured by the third resistor and a fourth resistor connected in series with the third resistor, and outputs a resistor divided voltage obtained by dividing a voltage of the horizontal synchronization signal through the third resistor and the fourth resistor to the image pickup section.

6. An endoscope system comprising: an image pickup section provided with a solid-state image pickup device and configured to obtain an examination image; a cable that transmits the examination image; and a processor that receives the examination image, performs image processing, and displays the processed image, the processor comprising:
a level limiting circuit that detects a clock signal for driving the image pickup section, the level limiting circuit being configured to output the clock signal when the clock signal is detected and output a signal whose output level is limited so as not to exceed a level of an input voltage standard of the image pickup section when the clock signal is not detected; and a peaking circuit that performs waveform correction of the clock signal outputted from the level limiting circuit.

* * * * *